US008868213B2

(12) United States Patent
Shan et al.

(10) Patent No.: US 8,868,213 B2
(45) Date of Patent: Oct. 21, 2014

(54) MICROLEAD FOR DETECTION/STIMULATION, IMPLANTABLE IN VENOUS, ARTERIAL OR LYMPHATIC NETWORKS

(71) Applicant: Sorin CRM S.A.S., Clamart Cedex (FR)

(72) Inventors: Nicolas Shan, Juvisy sur Orge (FR); Jean-Francois Ollivier, Villiers-le-Bacle (FR); Philippe D'Hiver, Chatillon (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/649,463

(22) Filed: Oct. 11, 2012

(65) Prior Publication Data
US 2013/0096658 A1 Apr. 18, 2013

(30) Foreign Application Priority Data
Oct. 14, 2011 (FR) ...................................... 11 59321

(51) Int. Cl.
*A61N 1/05* (2006.01)
(52) U.S. Cl.
CPC .......... *A61N 1/056* (2013.01); *A61N 2001/0585* (2013.01); *A61N 1/0529* (2013.01)
USPC ....................................................... 607/122
(58) Field of Classification Search
CPC ............... A61N 1/056; A61N 1/0573; A61N 2001/0585; A61N 1/05; A61N 1/0536; A61N 1/0568; A61B 5/0422
USPC .................................................. 607/44, 122
See application file for complete search history.

(56) References Cited

U.S. PATENT DOCUMENTS

| 5,246,014 | A  | * | 9/1993 | Williams et al. ............... 607/122 |
| 6,192,280 | B1 |   | 2/2001 | Sommer et al. |
| 7,047,082 | B1 |   | 5/2006 | Schrom et al. |
| 2006/0247751 | A1 |   | 11/2006 | Seifert |
| 2009/0157136 | A1 | * | 6/2009 | Yang et al. ....................... 607/17 |

(Continued)

FOREIGN PATENT DOCUMENTS

| EP | 2145648 A1 | 1/2010 |
| EP | 2455131 A1 | 5/2012 |
| WO | WO 2005/081681 A2 | 9/2005 |
| WO | WO 2005081681 A2 * | 9/2005 |

OTHER PUBLICATIONS

Foreign Search Report (Annexe Au Rapport De Recherche Preliminaire Relatif A La Demande De Brevet Francais No. FR 1159321 FA 756844), Jun. 21, 2012.

*Primary Examiner* — Rex R Holmes
(74) *Attorney, Agent, or Firm* — Foley & Lardner LLP

(57) ABSTRACT

A microlead implantable in a patient's venous, arterial or lymphatic networks for the detection and/or stimulation of tissue. The microlead has a diameter at most equal to 2 French (0.66 mm) and comprises at least one microcable (40) comprising a core cable (11) and an insulation layer (20) partially surrounding the core. The core is formed of a plurality of strands, and has a composite structure comprising a structuring material having high fatigue resistance, and a radiopaque material. A denuded area (30) is formed in the isolation layer (20) so as to form at least one electrode for stimulation detection. The microlead is shaped at the electrodes (30) according to at least one electrical contact and mechanical stabilization preshape, and has a gradual decrease of rigidity along the microlead between its proximal portion and its distal portion.

19 Claims, 7 Drawing Sheets

(56) References Cited

U.S. PATENT DOCUMENTS

2010/0049288 A1* 2/2010 Westlund et al. ............ 607/122
2010/0137928 A1* 6/2010 Duncan et al. .................... 607/5
2010/0211147 A1 8/2010 Schiefer et al.
2012/0130464 A1 5/2012 Ollivier

* cited by examiner

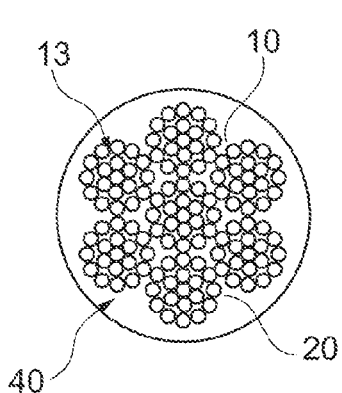
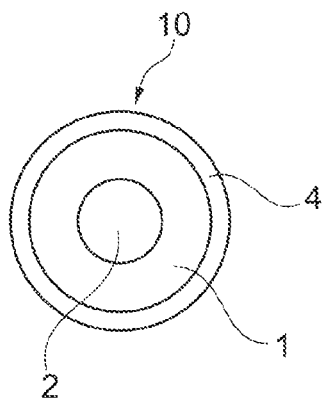
Fig. 12a    Fig. 12b
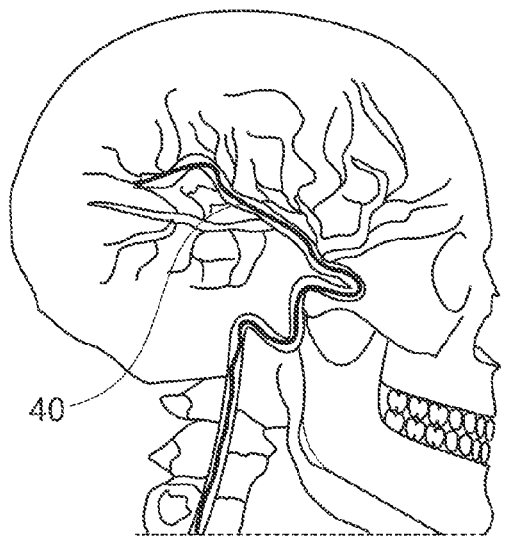
Fig. 12c

MICROLEAD FOR DETECTION/STIMULATION, IMPLANTABLE IN VENOUS, ARTERIAL OR LYMPHATIC NETWORKS

RELATED APPLICATIONS

The present application claims the priority date benefit of French Patent Application No. 11/59321 entitled "Microlead For Detection/Stimulation, Implantable in Venous, Arterial or Lymphatic Networks" and filed Oct. 14, 2011.

FIELD OF THE INVENTION

The present invention relates generally to the "active implantable medical devices" as defined by the Jun. 20, 1990 Directive 90/385/EEC of the Council of European Communities, which includes implantable devices that continuously monitor the cardiac rhythm of a patient and deliver if and as necessary to the patient's heart electrical pulses for stimulation (pacing), cardiac resynchronization, cardioversion and/or defibrillation, as well as neurological devices, cochlear implants, drug, infusion devices, implantable biological sensors, etc. The present invention relates more specifically to a microlead for detection/stimulation for implantation in the venous, arterial or lymphatic networks of a patient.

BACKGROUND

Implantable medical devices typically have a housing generally designated as the "generator", which is electrically and mechanically connected to one or more intracorporeal "leads" provided with electrodes that are intended to come into contact with the patient's tissues on which it is desired to apply the aforementioned electrical pulses and/or collect an electrical signal: e.g., the myocardium, nerve, or muscle tissue.

The current principle of electrical stimulation of tissue (hereinafter, stimulation is used in its generic sense of delivering an energy pulse to tissue rather than in a context of delivering an energy pulse suitable for pacing) is based on a device, usually called a "lead", which is an object implanted through various venous, arterial or lymphatic vessels, and whose function is to transmit an electrical signal between a generator at a proximal end of the lead target and a tissue at a distal end of the lead while ensuring the following properties:

Ease of implantation by the physician in a vessel network of the patient, and especially ease of advancing the lead into the vessel(s) by pressure, to make the lead follow the tortuous paths and passing side branches in the vessel network, and to transmit torques from one end of the lead to the other;

Detectable by X-rays to allow the doctor to easily navigate through the network of vessels guided by X-ray fluoroscopy;

Atraumaticity of the lead in the veins, which requires a flexible structure and the lack of a rigid transition or sharp edges;

Ability to transmit an electrical signal to tissues and to make stable monopolar or multipolar electrical measurements;

Biocompatibility with living tissue for implantation in the long term;

Ability to connect to an implantable device generator or other source of electrical signals to be transmitted;

Ability to be sterilized (e.g., by gamma radiation, temperature . . . ) without damage;

Biostability, especially corrosion resistance in the living environment and resistance to mechanical fatigue stress related to patient and organs movement;

Compatibility with magnetic resonance imaging (MRI) which is, particularly important in neurology.

The current architecture of leads that meet these needs can be summarized as a generally hollow structure that allows passage of a stylet or a guidewire, and includes components such as insulated current carrying conducting cables or "lines", connected to mechanical electrodes for ensuring electrical conductivity, radiopacity, etc. These leads therefore require a complex assembly of a large number of parts, of associated wires and insulating elements, creating substantial risks of rupture given the long-term mechanical stresses they face.

Examples of such known leads are given in U.S. Pat. Nos. 5,246,014, 6,192,280, and 7,047,082.

One of the challenges in making suitable leads includes the management of stiffness gradients related to the mechanical components used, which strongly affect the implantability of the lead and its long term strength (fatigue endurance) properties.

In addition, to seal the inner lumen of the leads, for which the blood would degrade the performance during implantation and in the long term, valves and other complex devices are used, with significant associated risks.

Other difficulties may also arise in terms of fatigue of the assemblies. Indeed, any stiffness in a transition area is likely to induce a risk of fatigue, difficulty in sterilization because of the presence of areas that are difficult to access, and problems of mechanical strength at junctions of the conductors with the distal electrodes and with the proximal connector to the generator.

Moreover, the clinical trend in the field of implantable leads is to reduce their size to make them less invasive and easier to handle through the vessels.

The current size of implantable leads is typically on the order of 4 to 6 French (1.33 to 2 mm) in their active part, that is to say, the most distal end bearing the electrode(s)—even if the lead body, in the less distal end, uses conductors with a smaller diameter, for example, as described in U.S. Pat. No. 5,246,014 above, which, at the lead body, certainly includes a conductor the diameter of which does not exceed 1 French (0.33 mm), but the overall diameter of the distal end active part at the location of the screw anchor is several French. However, it is clear that reducing the size of the leads would increase their complexity and impose technical constraints generating risks.

On the other hand, such a reduction, to less than 2 French (0.66 mm), for example, would open up prospects for medical applications in various fields ranging from cardiology to neurology in the presence of a venous, arterial or lymphatic system such as the cerebral venous system or the coronary sinus venous system.

Today, the electrical stimulation technology has led to major advances in the field of neuromodulation and stimulating target areas of the brain to treat Parkinson's disease, epilepsy and other neurological diseases. One could imagine implementing this type of technology to address new areas difficult to reach today, by using small size stimulation leads, or "microleads", having great strength to ensure long-term biostability. Such a technique would allow a less invasive approach to these therapies and an especially superior efficacy of treatments.

It would be possible to connect one or more microleads through the considered vessel network until the target location. Their implantation could be done, because of their small size, by today's guiding devices used in interventional neuroradiology for the release of stents (spring coils) in the treatment of intracranial aneurysms.

OBJECT AND SUMMARY

It is therefore, an object of the present invention to provide a microlead that is consistent with the general properties of implantable leads as listed above, with reduced complexity and, therefore, final cost.

Advantageously, a microlead has a size making it possible to achieve implantation in very small veins, now inaccessible with larger conventional devices. The microlead of the present invention should also greatly facilitate navigability in venous, arterial or lymphatic networks vessels because of its flexibility, enhanced by its small size.

Broadly, the present invention is directed to a lead of the general type disclosed in U.S. Pat. No. 5,246,014 A mentioned above, comprising a microcable having a diameter of most equal to 2 French (0.66 mm), comprising: an electrically conductive core cable having a diameter of at most equal to 0.50 mm, formed of a plurality of strands, each strand having a diameter of at most equal to 40 µm, the core cable comprising a structuring material having a high fatigue resistance, such as stainless steel, cobalt alloy, precious metal, titanium or nitinol (NiTi) alloy; and a polymeric insulation layer partially surrounding the core cable having a thickness of at most equal to 30% of the diameter of the core cable.

The microlead of the present invention has a distal end containing an active part, comprising a microcable having a diameter at most equal to 2 French (0.66 mm). The microcable includes a core cable that is a composite structure formed of at least said structuring material and a radiopaque material, the radiopaque material constituting at least about 0.008 mm² of the core cable cross section and in a proportion of at most equal to 50%. In addition, at least one denuded area is formed in the polymeric insulation layer so as to form at least one electrode. The electrode(s) have a cumulative total surface area of at most equal to 20 mm². Further, the microlead is constructed to have a decrease in rigidity along the microlead length between its proximal and distal end, preferably a gradual decrease.

The microlead may be rectilinear or, preferably, shaped at the electrodes according to at least one predetermined shape for electrical contact and mechanical stabilization.

As first appreciated by the inventors, it should be understood that with a diameter not exceeding 0.50 mm, the multiwire strand forming the core cable of the microlead according to the present invention has high flexibility, which is favorable to its manipulation by the physician, especially during its implantation, for example, when it is introduced into vessel networks with high tortuosity and numerous branches and when injuries that could occur with much more rigid leads, incompatible with the tissues, should be avoided.

On the other hand, the choice of a multiwire stranded structure for the core cable composed of very small wires having an individual diameter that is not more than 40 µm, preferably between 20 and 40 µm, provides critical increased resistance to mechanical fatigue of the core cable due to patient and organ movement, knowing that the ultimate tensile strength in bending of a wire is substantially inversely proportional to its diameter. In order to strengthen this important biostability property, it is advantageous that the wires themselves are made of a material whose resistance to structuring fatigue is intrinsically high, such as the stainless steel, cobalt alloys, titanium and nitinol (NiTi) materials mentioned above. In addition to these metals that are responsible for ensuring the mechanical integrity of the cable core, a radiopaque material is added for making the microlead visible to X-rays when it is put in place by the physician. The radiopaque material may be selected from tantalum (Ta), tungsten (W), iridium (Ir), platinum (Pt), gold (Au) and their alloys.

In one embodiment, the composite structure of the core cable of the invention thus obtained may be constituted by composite strands, with at least one structuring material and one radiopaque material, or by strands made of a structuring material and by strands made of a radiopaque material. The plurality of strands advantageously comprises from 15 to 300 strands.

To make electrical contact with the tissues and transmit the electrical signal, the present invention discloses a solution to the electrical junction problem by using the core cable itself to form the electrodes of the microlead. This is achieved by establishing denuded areas in an insulation layer surrounding the core cable. In one embodiment, the insulation layer, preferably made of a fluoropolymer, has a thickness that does not exceed 30% of the diameter of the core micro-cable. This dimension is selected to avoid a staircase effect at the edge of electrodes (i.e., the exposed core cable) that could interfere with making adequate electrical contact with tissue.

The microlead of the present invention includes means for gradually decreasing stiffness of the microlead (i.,e., the rigidity decreases from the proximal end to the distal end). The rigidity decrease is provided to facilitate the implantation of the microlead through its ability to be pushed by the surgeon into the patient's vessels. As discussed in detail below, the means for gradually decreasing stiffness can be, in accordance with embodiments of the present invention, a stack of layered tubes placed one inside the other, or a series of iso-diameter tubes having different rigidities appropriately ordered and strung together adjacent one another along the core cable.

In one embodiment, once the microlead is in place, it is stabilized in position by having a three dimensional S or spiral preshape, which preshape also provides a permanent electrical contact of the electrodes with tissue. Advantageously, the microlead further includes local reinforcing means for reinforcing a localized area or length of the microlead, e.g., to provide an angulation or a preshape.

In one embodiment, to limit the heating of the core cable by the skin effect during an MRI examination, the strands comprise an outer layer of material having a low magnetic susceptibility, i.e., less than $2\,000 \times 10^{-12} m^3 mole^{-1}$. Such low magnetic susceptibility material may be selected from among, tantalum (Ta), titanium (Ti), rhodium (Rh), molybdenum (Mo), tungsten (W), palladium (Pd), gold (Au) and their alloys.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 10b is a sectional view of the distal section of the microlead of FIG. 10a;

FIG. 10e is a perspective view illustrating an implantation of the microlead of

Figure 10A:
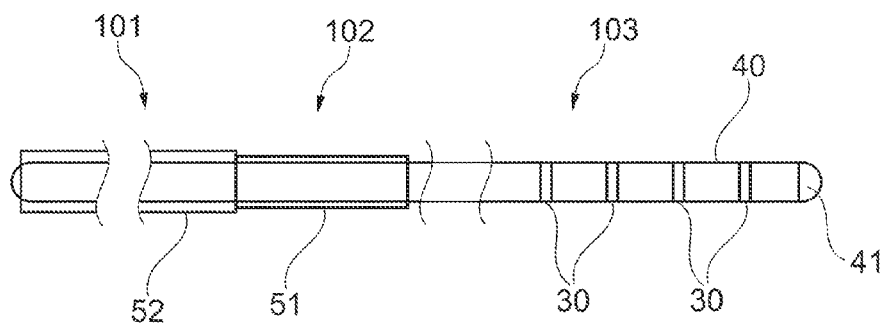
FIG. 10a is a side view of a first embodiment of a microlead of the present invention.
Figure 11A:
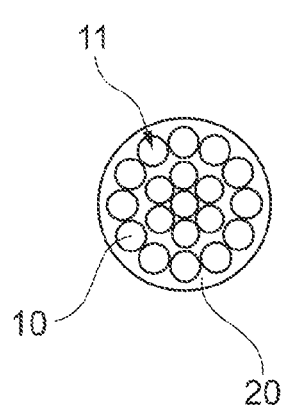

FIG. 10a in the coronary vein network;

FIG. 11a is a sectional view of a second embodiment of a microlead in accordance with the present invention.

Figure 11B:
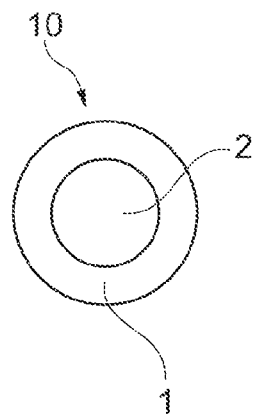
Figure 11C:
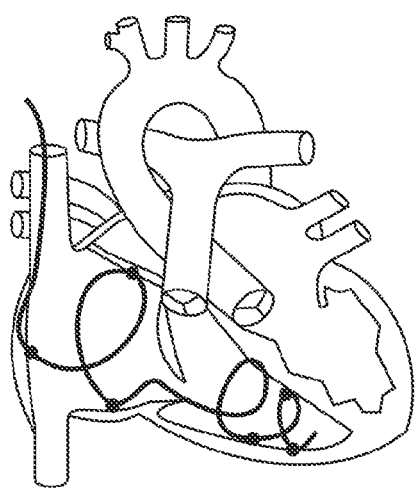
Figure 11D:
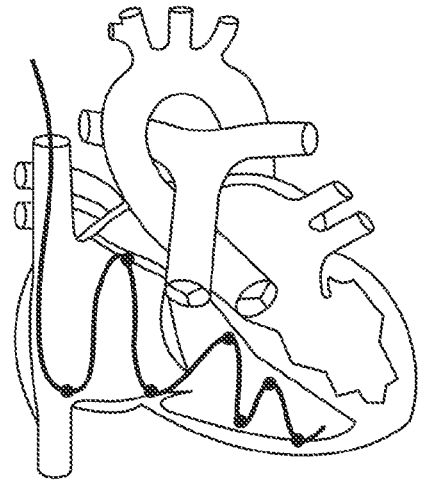

FIG. 11b is a sectional view of a unit strand of the core cable of the microlead of FIG. 11a;

FIGS. 11c and 11d are perspective views showing implantations of the microlead of FIG. 11a in a cavity of the heart;

FIG. 12a is a sectional view of a third embodiment of a microlead according to the present invention;

FIG. 12b is a sectional view of a single strand of the core cable of the microlead of FIG. 12a; and FIG. 12c is a sectional view of an exemplary implementation of the microlead of FIG. 12a in brain tissue.

DETAILED DESCRIPTION

With respect to the drawings FIGS. 1-12, various preferred embodiments in accordance with the present invention will now be discussed. The microleads of the invention are referred to as stimulation microleads and intended to be implanted in venous, arterial or lymphatic networks of a patient, e.g., a human, and whose diameter does not exceed 2 French (0.66 mm). They are constituted, in their active part, by a microcable formed of a conductor core cable at least partially surrounded by an insulation layer defining at least one stimulation electrode.

The useful lifetime of an active implantable medical device is a fundamental parameter that must be taken into account when designing any medical device, especially stimulation microleads, the subject of the present invention. Indeed, the heart beats and the organ motion induce on such devices bending deformations that must be accommodated and controlled.

In general, for a cylindrical wire of diameter d, the bending deformation can be characterized by the ratio $\epsilon = d/D$ wherein D is the diameter of the curvature imposed on the wire by the bending stress. This bending stress, for example, due to a heartbeat, may be experienced by the strand for $400 \times 10^6$ cycles over a period of 10 years, potentially resulting in material fatigue that can cause a wire to break and limit its lifespan.

Thus, a stimulation microlead through the venous system, for example, may face deformation of a curvature greater than that of a normal lead to the extent that it must follow the deformation of the veins, causing a bigger stress and making its resistance to fatigue more difficult.

To increase the fatigue tensile strength of microleads, the inventors hereof have discovered that it is therefore advantageous to select for the core cable a multiwire structure in the form of a strand of a plurality of conductive strands of relatively small diameter d. The reduction in diameter of the individual strands makes it possible to reduce the stress applied to each of them and thus increase the fatigue performance of the structure of the strand. For a given material, it is possible to define a maximum deformation $\epsilon_{Max}$ corresponding to the limit of fatigue resistance for a number of deformation cycles, for example, equal to about $100 \times 10^6$.

The choice of a material constituting the framework of the core cable, herein called a "structuring material", must meet several criteria. It must be a material whose mechanical properties are known for long-term implantable applications and present a maximum deformation $\epsilon_{Max}$ greater than that which a single strand is likely to undergo, while remaining compatible with the technical feasibility and cost of a very small diameter strand. For example, for a cobalt alloy such as MP35N having a maximum deformation $\epsilon_{Max}$ of $5.10^{-3}$ for $100 \times 10^6$ cycles and for a diameter D of curvature of 7 mm, the diameter of the strand unit must be less than about 35 µm. Thus, a strand of diameter 20 µm easily withstands this stress, while a strand of diameter 40 µm risks generating a break before reaching $100 \times 10^6$ cycles. Note that the NiTi alloys exhibit a greater maximum deformation $\epsilon_{Max}$, from 5 to $9 \times 10^{-3}$, thus providing even wider opportunities.

In summary, it is proposed by the present invention to use as a structuring material stainless steel, a cobalt alloy of the MP35N series, a precious metal, titanium or a NiTi alloy, having a high fatigue resistance, to form a multiwire structure with a diameter d of the strands not exceeding 40 µm. This size is selected because it is an average ensuring maximum resistance to fatigue failure under extreme conditions of stress to which such structures can be submitted.

In a preferred embodiment, strands having a diameter of between 20 and 40 µm will be considered optimal, the larger diameters not meeting the identified fatigue resistance for the useful life, and the smaller dimensions possibly causing problems of technical feasibility and cost in the manufacture and assembly process.

To ensure adequate visibility for X-ray fluoroscopy during microlead implantation, it is necessary to introduce along the core cable a minimal amount of a radiopaque material. The difficulty here is to reconcile the needs for fatigue resistance of the cable with the radio-opacity and resistance to corrosion. Indeed, most materials used for their X-ray visibility, namely tantalum (Ta), tungsten (W), iridium (Ir), platinum (Pt), gold (Au) and their alloys, do not generally have high resistance to fatigue. Therefore, as the inventors here discovered, it is advantageous to provide a composite structure, referred to herein as a composite cable, in which a radiopaque material is added to the structuring material within at least some of the plurality of individual strands.

Given the sensitivity of X-ray equipment used to detect radiopaque material, it should be understood that a minimal presence of radiopaque material in the composite structure is needed, and under the current x-ray equipment sensitivity limits, the amount is equal to an area of 0.008 $mm^2$ in the core cable section, but with the proportion of radio-opaque material not exceeding 50%, in order not to degrade the mechanical properties of strands provided by the structuring material.

Figure 1A:
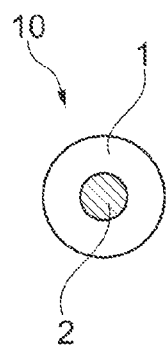
FIGS. 1a to 1d are sectional views of strands made of a structuring material and of a radiopaque material.
Figure 1B:
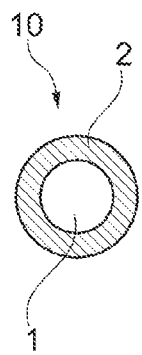
Figure 1C:
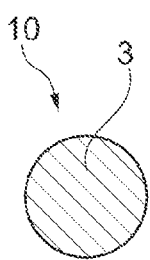
Figure 1D:
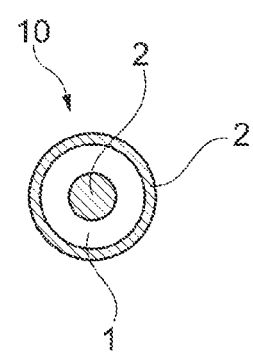

As shown in FIGS. 1a to 1d, the composite cable structure of the core cable is made of composite strands, of at least one structuring material 1 and of at least one radiopaque material 2. Specifically, FIG. 1a shows a strand with the structuring material 1 being outside the wire and the radiopaque material 2 being inside. Conversely, in the strand illustrated in FIG. 1b, the structuring material 1 is inside and the radio-opaque material 2 is on the outside. The strand shown in FIG. 1c is made of an alloy 3 of a structuring material and of a radio-opaque material. Finally, the structure of the strand shown in FIG. 1d is more complex, with two outer and inner sections of radio-opaque material 2 surrounding an intermediary section of structuring material 1.

Figure 2A:
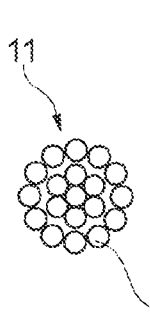
FIGS. 2a to 2f are cross sectional views of the core cables having strands shown in FIGS. 1a to 1d.
Figure 2B:
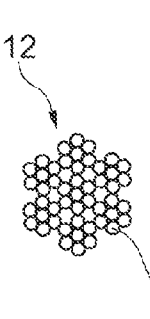
Figure 2C:
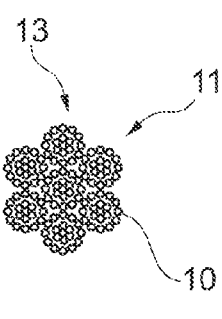
Figure 2D:
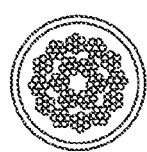
Figure 2E:
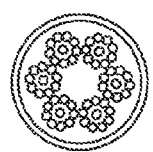
Figure 2F:
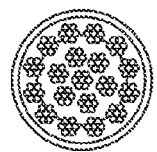

The strands 10 thus obtained can be twisted together to form a core cable for the microlead. In FIG. 2a, a strand 11 of nineteen individual strands 10 is shown. The strand 12 illustrated in FIG. 2b is formed by the assembly of seven groups of seven strands 10. FIG. 2c shows a strand 13 of seven groups of nineteen strands assembled using the strand 11 of FIG. 2a. For example, each group of nineteen strands may be twisted together to form a group, and then the seven groups are twisted together to form the core cable. Finally, more complex structures are illustrated in FIGS. 2d-2f.

Figure 3:
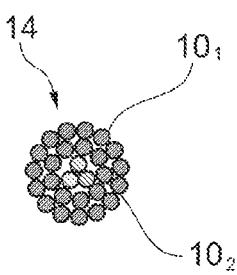
FIG. 3 is a sectional view of a core cable made of structuring strands and of radiopaque strands.

According to the embodiment illustrated in FIG. 3, core cable 14 has a composite structure made not at the level of the strands but at the core cable itself. In this embodiment, strands $10_1$ made of a structuring material surround strands $10_2$ made of a radiopaque material.

Regarding the number of wires per strand, one can calculate that for a diameter of 40 μm and for a proportion of radiopaque material of 50% occupying a section of 0.008 $mm^2$, the total number of strands, all materials combined, is on the order of fifteen wires. Conversely, for a strand diameter of 15 μm and a proportion of radio-opaque material occupying 15% of the same section, the total number of strands is approximately 300 strands.

Another important physical characteristic for a microlead is its flexibility. It is this property which indeed allows the stimulation lead to cross a tortuosity of small radius and ensure atraumaticity of the lead avoiding perforation of the veins in which it circulates. To ensure atraumaticity, the tip of the microlead is preferably rounded in a hemisphere shape to minimize any risk of perforation.

By comparison with the existing guidewires used in similar applications, the applicant has been able to establish that an outer diameter of the core cable of 0.50 mm provides an adequate level of flexibility and of compatibility with living tissue.

In general, the compatibility of implantable devices with modern medical techniques for imaging, such as MRI, is essential to ensure optimal treatment of the patient. Indeed, because of its globally metallic structure, the microlead is at risk of heating due to the currents induced by the well known "skin effect" on the outside the individual strands under the action of applied magnetic field. Given the small diameter of strands, however, they nevertheless favour heat dissipation which reduces the heating effects due to MRI.

In addition, the thermal energy stored by the materials, already limited in volume, can be further reduced if the individual strands are coated with an outer layer of material having a low magnetic susceptibility (magnetic susceptibility is the ability of a material to magnetize under the action of an external magnetic field). The materials most favorable in this application are those whose magnetic susceptibility is less than $2000 \times 10^{-12}$ $m^3.mole^{-1}$, including tantalum (Ta), titanium (Ti), rhodium (Rh), molybdenum (Mo), tungsten (W), palladium (Pd), gold (Au) and their alloys.

Figure 5:
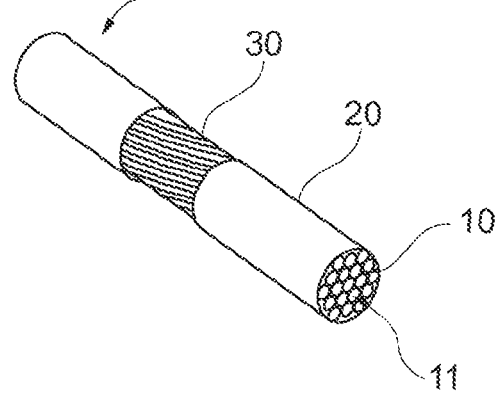
FIG. 5 is a perspective view of a microcable with a totally denuded zone of the insulation layer.

Regarding the transmission of electric current to the tissues, the concept adopted by the present invention is not to provide separate electrodes structures coupled to the current carrying wires, but, as shown in FIG. 5, to use the conductor core cable 11 itself to form the electrodes by partly surrounding the core cable with a layer of insulation polymer 20. An electrode 30 is thus formed by a denuded area formed in the insulation layer 20 and exposing underlying cable core 11. This coating technique offers electrode 30 a contact sufficient to ensure the electrical stimulation of tissue.

In the preferred embodiment, isolation layer 20 covers all of the conductive structure of the core cable 11, except at the denuded areas establishing the electrode zones distributed along the microcable thus constituted.

Preferably, the thickness of the isolation layer 20 does not exceed 30% of the outside diameter of the core cable 11. This dimension is selected to avoid the staircase effect on the edge of electrode, wherein the insulation thickness might possibly prevent contact of the electrode with tissue.

The characteristics required for isolation layer 20 are:
Fatigue resistance,
Electrical isolation,
Long-term biocompatibility,
Biostability, and
Possibility of transformation and implementation consistent with the conductor of the core cable.

The materials that can be used in this context include, for example:
Polyurethanes (PU),
Polyesters (PET),
Polyamides (PA),
Polycarbonates (PC),
Polyimides,
Fluorinated polymers,
The polyether-ether-ketone (PEEK),
Poly-p-xylylene (parylene), and
Polymethacrylate of methyl (PMM).

However, the preferred materials are those with high chemical inertness such as fluoropolymers, which also have very good insulation properties. These compounds include:
PTFE (polytetrafluoroethylene),
FEP (perfluorinated propylene),
PFA (perfluoroalkoxy copolymer resin),
THV (tetrafluoroethylene, hexafluoropropylene, vinylidene fluoride),
PVDF (polyvinylidene fluoride),
EFEP (fluorinated ethylene propylene ethylene), and
ETFE (ethylene tetrafluoroethylene).

The methods for making the insulation layer of the core cable are conventional and many, depending on the materials used and include, for example:
Co-extrusion on the conductor, for PU, PA, PEEK, polyimides and fluoropolymers;
Deposit by immersion in a solution, for PU, PA and polyimides;
Heating of a heat-shrinkable tube, for PET and fluoropolymers;
Chemical deposition using a gas, for parylene;
Plasma processing to improve adhesion between the layers.

Figure 6:
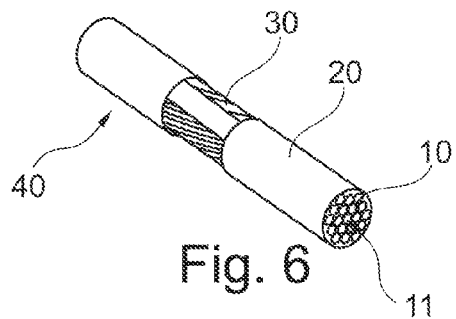
FIG. 6 is a perspective view of a microcable having a partially denuded zone of the insulation layer.
Figure 7A:
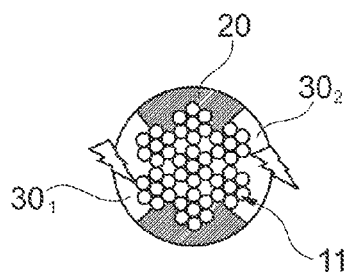
FIGS. 7a and 7b are sectional views of microcables with zones of insulation layer partially denuded.
Figure 7B:
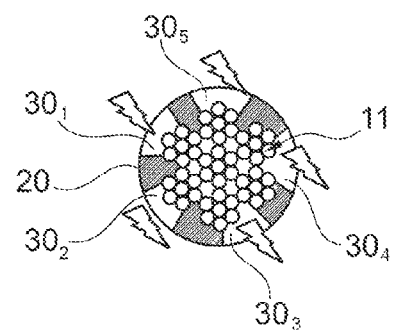
Figure 8:
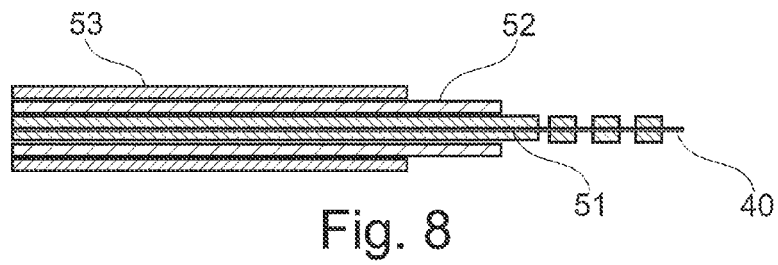
FIG. 8 is a sectional view of a microlead having a stack of tubes with a rigidity gradient.

During the implementation of these methods, the denuded areas establishing the electrode areas can be defined in any number of ways, for example, by deposition of insulating layers separated from each other, or by partial denuding of an insulation layer deposited on the entire cable. This denuding may be carried out in any conventional manner, for example by laser or photo ablation or chemical etching or mechanical stripping. As shown in FIGS. 6 and 7a, 7b, this technique allows for establishing partial openings of any of a number of defined shapes. In particular, FIGS. 7a and 7b show a microcable respectively with two denuded areas $30_1$, $30_2$, and five denuded areas $30_1$, $30_2$, $30_3$, $30_4$, $30_5$.

Advantageously, the electrode areas 30 distributed along the microcable have a combined surface area not exceeding 20 mm$^2$, for example, in the form of 40 electrodes each having 0.5 mm$^2$ or 20 electrodes each having 1 mm$^2$. It should be understood that the surface area depends upon the intended application for the microlead as well as on the intended electrical performances of associated equipment.

In a preferred embodiment, in order to limit power consumption of the generator, it is preferable to provide electrodes 30 having a surface area of at most equal to 0.5 mm$^2$, thereby increasing the local current density.

If necessary, the microcable optionally may comprise at the electrodes a strengthening of the corrosion resistance, preferably obtained by adding a very high resistance dedicated coating. The corrosion resistance can also result from the choice of a structure wherein the noble metal of radiopaque material forms an outer layer encasing a core of structuring material.

A first embodiment is to apply a sub-micron chemical or electrochemical deposit (i.e., a layer less than 1 μm thick) of a noble material, such as those mentioned above for use as radiopaque materials.

A second embodiment is to make a composite tube such as a DFT tube (Drawn Filled Tube), with an additional layer of from 1 to 2 μm of noble metal.

A third embodiment is to make a carbon deposit such as Carbofilm (registered trademark of Sorin CRM s.r.l.) to obtain a corrosion protection and good performance in terms of hemocompatibility and biocompatibility.

If necessary, the outer surface of the insulation layer near the electrodes optionally may contain an anti-inflammatory drug such as steroid. In this case, a very thin layer of steroid is deposited at the end of the manufacturing process by chemical grafting or by polymer crosslinking, for example, a biodegradable polymer such as PLAGA (polylactic co-glycolic acid) or PLA (polylactic acid). It is also conceivable that an anti-inflammatory drug can be contained in the material forming the insulating layer.

Finally, the microlead is completed at its proximal end by a connector connected to the generator of the implantable device.

According to one preferred embodiment of the present invention, due to the small size of the microlead, it can be preshaped at the electrodes to facilitate electrical contact with the tissues, and also to mechanically stabilize the microlead once implanted in the vessels. The preshapes may be obtained by suitable forming of the metal or polymer materials of the lead, for example, by conventional heat processing techniques.

Figure 4A:
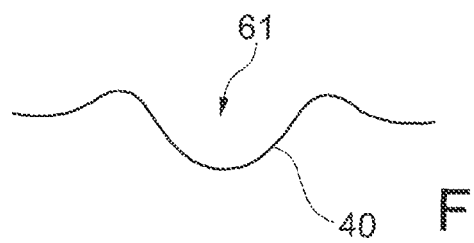
FIGS. 4a to 4d are side views of preshapes of microleads in accordance with the invention.
Figure 4B:
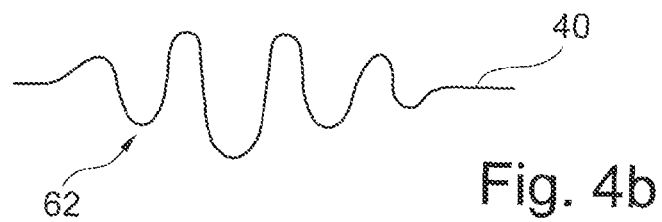
Figure 4C:
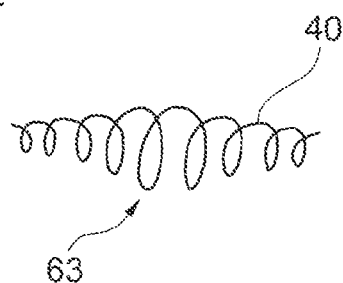
Figure 4D:
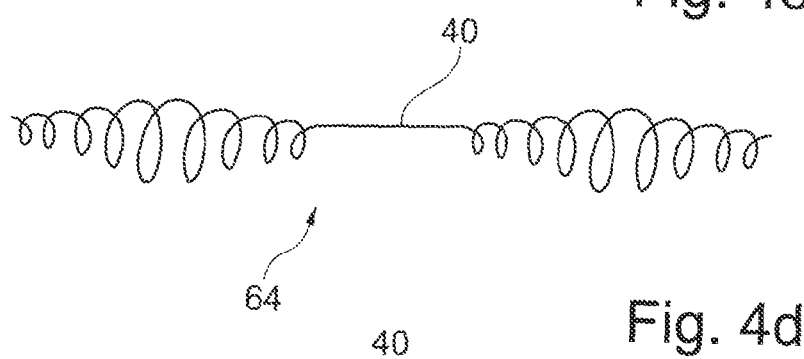

With reference to FIGS. 4a to 4d, several preferred embodiments of the preshape are illustrated: The preshapes shown in FIGS. 4a and 4b have a planar S or almost sinusoidal-like undulation configuration of multiple half cycles while the preshapes shown in FIGS. 4c and 4d are configured in a three dimension, single or double, spiral configurations.

According to another aspect of the present invention, a defining characteristic of a microlead is that it can be easily manipulated by the physician during implantation. It is also important to minimize the transitions of stiffness along the lead to minimize stress concentrations can lead to fatigue embrittlement of the device. Nevertheless, some stiffening is required because an excessively flexible microlead limits thrust manipulation.

In accordance with the present invention, these difficulties are solved by a staged stiffening, made possible by means for gradually decreasing the stiffness provided between the proximal and distal ends of the microlead. This makes it possible to manage the progressive rigidity gradient along the lead in order to ensure, on the one hand, a non-traumatic flexible distal portion to pass through the tortuosities and, on the other hand, a more rigid proximal portion to transmit the thrust exerted by the physician using appropriate inserting devices.

In the example in FIG. 11, the means for gradually decreasing the stiffness are implemented as a layered stack of three tubes 51, 52, 53 fitted into each other on the microcable 40. Tube 51, 52 and 53 are preferably PET (polyethylene terephthalate) tubes, for example, having a thickness of 5 to 20 μm.

Thus, the rigidity at the proximal end of the lead in this embodiment can be fifty times greater than the rigidity at the distal end, without requiring the addition of additional mechanical part. The robustness of the system is also greatly increased.

In an alternative embodiment, the means for gradually decreasing the stiffness can be implemented as a series of isodiameter tubes of progressively decreasing stiffness, welded together. However, this technique generates risks of breaking at the welds between the tubes. In yet another embodiment, a coating of a single layer having a variable thickness and rigidity can be applied, as in a dip coating and controlled drawing process.

Figure 9:
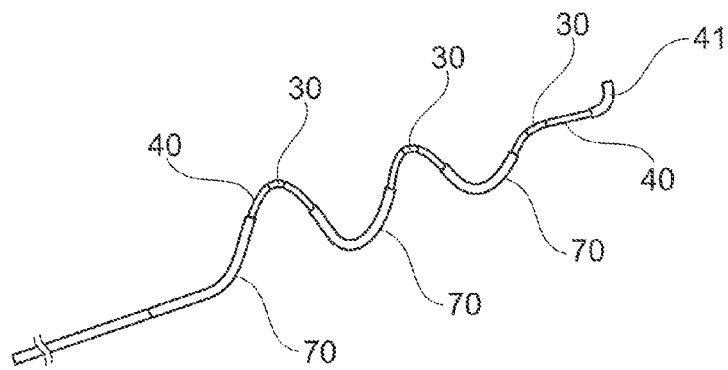
FIG. 9 is a perspective view of a microlead equipped with a local reinforcement device.

With reference to FIG. 9, another embodiment of the present invention is illustrated, including a local reinforcement of the microlead through a series of tubes 70 for, regardless of the insulation, reinforcing a preshape or an angulation necessary for the desired function, thereby giving the microlead a desired specific shape. The end 41 of the microlead may also be thermoformed by this type of method. This solid structure, without crevices, or weld seams, has the important advantage of being more easily sterilizable compared to conventional leads. This reduces the risk of material degradation of the microlead due to too aggressive a sterilization process.

A description of specific embodiments of the microlead of the invention, for implantation in different body sites, follows.

EXAMPLE 1

Figure 10B:
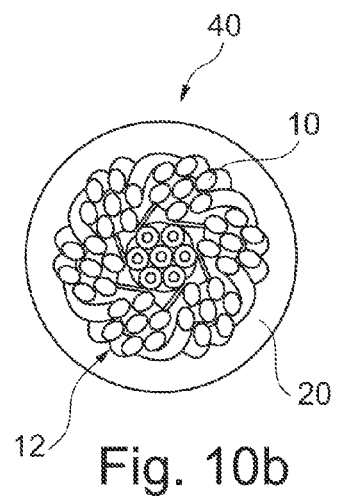
Figure 10C:
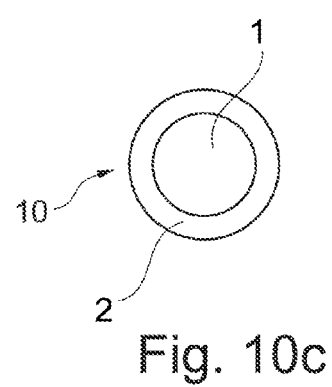
FIG. 10c is a sectional view of a unit strand of the core cable of the microlead of FIG. 10b.

FIGS. 10a to 10e illustrate one exemplary embodiment of a microlead according to the present invention for implantation in a vein in the coronary sinus. The microlead shown in FIG. 10a includes a microcable 40, a sectional view of which is shown in FIG. 10b. Core cable 12 of microcable 40 is formed of composite individual strands 10, as shown in FIG. 10c, of a core 1 made of a structuring material, here an MP35N alloy with a diameter of 33 μm, and an outer shell having a thickness a 5 μm of Pt/Ir 90/10 as radio-opaque material 2. The ratio between the materials is 75% for the core and 25% for the outer shell. This simple structure provides good fatigue strength and resistance to corrosion due to the presence of platinum.

Cable 12 with a core of 49 strands is necessary to obtain a platinum apparent surface area of 0.011 mm2, sufficient to ensure good visibility under x-ray fluoroscopy. The conductor core cable 12 then has a diameter of 0.30 mm, which makes it sufficiently flexible for intravascular use via the coronary sinus for example.

With reference to FIG. 10b, cable 12 is coated with a 25 μm thick layer 20 of insulation such as ETFE for good insulation, compatible with an extrusion line, for a final outer diameter of 0.35 mm in the distal portion 103 of the microlead.

With reference to FIGS. 10a and 10b, openings 30 forming electrodes are formed by laser ablation in the distal portion 103 on a surface area of 0.5 mm², to minimize power consumption. Heat shrink PET tubes 51 and 52 are respectively placed in an intermediate zone 102 and in the proximal portion 101, at 25 cm and 45 cm from the distal tip 41 of the lead, whose total used length varies between 90 and 120 cm.

Figure 10D:
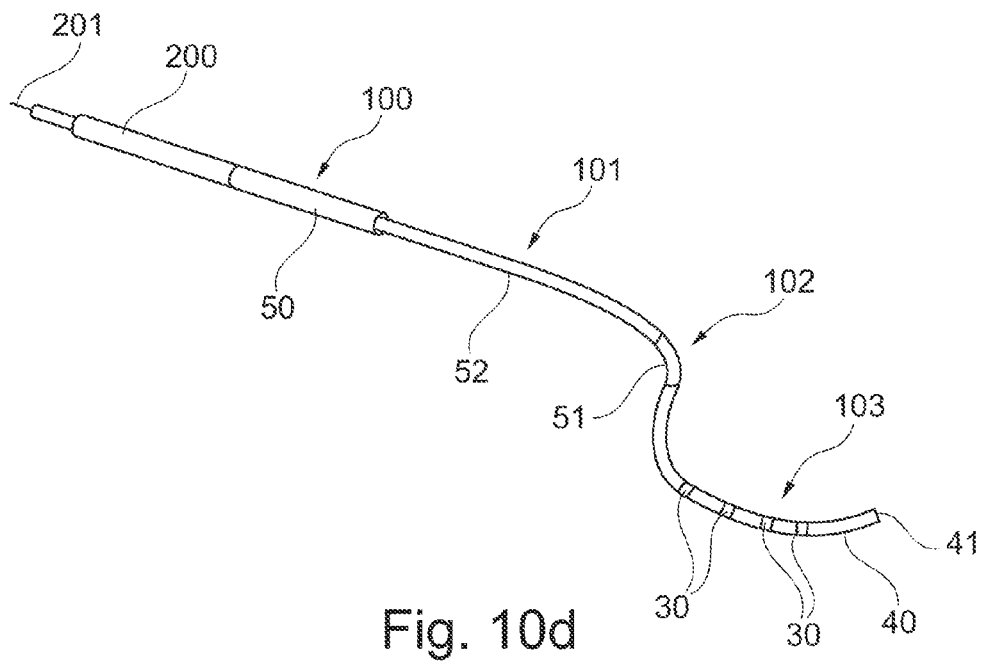
FIG. 10d is a perspective view of the microlead of FIG. 10a equipped with an IS-1 connector.

The entire structure of the microlead is illustrated in FIG. 10d, on which one can see that the proximal portion 101 terminates with a transition zone 100 formed by a polyurethane tube 50 connected to an industry standard IS-1 connector 200 which end is provided with a terminal 201 for electrical connection to the implantable generator.

Figure 10E:
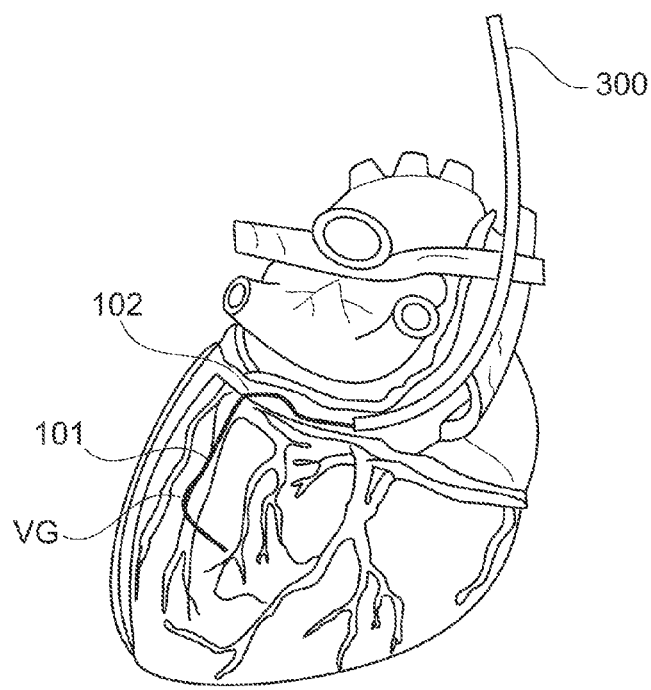

A method of implantation of such a microlead, shown in FIG. 10e, is to place the intermediate portion 102 in the coronary sinus and the distal portion 103 with multiple electrodes 30 in the veins of the coronary network, to stimulate the left ventricle VG. This is done using a catheter 300 that can be removed by cutting with a cutting tool (slitter), as conventionally used for the implementation of conventional leads.

EXAMPLE 2

A second embodiment of a microlead for implantation in a heart chamber, e.g., a right cavity, is shown in FIGS. 11a to 11d.

This microlead includes a microcable 40, a sectional view of which is shown in FIG. 11a. Core cable 11 of microcable 40 is formed of individual composite strands 10, as shown in FIG. 11b, a tantalum core 2 as a radiopaque material, and an outer shell 1 of structuring material, here nitinol. The ratio between the materials is 25% for the core and 75% for the outer shell. This simple structure provides external elasticity and good radiopacity provided by the inner core.

It should be noted that using nitinol has an advantage of presenting an important shape memory, which is particularly favourable to establishing an effective electrode contact in a large cavity.

Core cable 11 is formed of nineteen strands 10 as is necessary to obtain an apparent platinum surface area of 0.010 mm², sufficient to ensure good visibility under x-ray fluoroscopy. Conductor core cable 11 has a diameter of 0.20 mm, which gives it the flexibility for intracavitary use, e.g., the right ventricle and/or right atrium in particular.

Cable 11 is covered with a layer 20 of FEP insulation having a thickness of 25 µm for good insulation. It is compatible with an extrusion process, for a final outer diameter of 0.25 mm in the distal portion the microlead.

In this embodiment, it is possible to use a reinforcing structure such as very thin polyimide or PEEK to keep the superelastic properties of nitinol. In this case, a coating of a material such as Carbofilm (registered trademark) is applied on the entire microcable having a superior corrosion resistance, as well as an increased biocompatibility. This type of coating, less than 1 µm thick, does not change the electrical properties of the electrode while substantially improving the properties of surface compatibility with blood.

In addition, by appropriate processing, it is possible to give the lead a configuration allowing it to comply with the heart chamber based on the needs of stimulation and associated anatomy. FIGS. 11c and 11d show two possible conformations of the lead for stimulation of the right cavities.

EXAMPLE 3

A third embodiment of a microlead in accordance with the present invention, for implantation in the brain cavities, is shown in FIGS. 12a to 12c. In this example, a very good radiopacity is required, as well as flexibility and a very small diameter. Moreover, for this type of product, the MRI compatibility is essential.

The microcable 40 of this embodiment shown in FIG. 12a includes a core cable 13 formed of composite individual strands 10 formed, as shown in FIG. 12b, of a tri-layer wire comprising (i) a core 2 of radiopaque material, tantalum here, (ii) an intermediate layer 1, here titanium, as the structuring material, and (iii) an outer casing 4 of palladium to minimize the skin effects and achieve better structural compatibility with MRI. The ratio between the three materials is 30% Ta/65% Ti/5% Pd. This structure, although less fatigue resistant at the strand 10, is compensated by a unit diameter of 16 µm, that is less mechanically stressed.

A core cable 13 of 133 strands (7×19) is required to obtain an apparent platinum surface area of 0.010 mm², sufficient to ensure good visibility under x-ray fluoroscopy. The conductor core cable 13 then has a diameter of 0.25 mm, very flexible, for intracerebral use.

The cable 13 is covered with a layer 20 of FEP insulation, more mechanically flexible, of a 25 µm thickness, allowing a good insulation and compatible with an extrusion process, for a final outer diameter of 0.30 mm in the distal end of the microlead.

A block amide polyether Pebax (registered trademark of ARKEMA, Cf.http://www.pebax.com/sites/pebax/en/home.page) may be associated with the isolation layer 20 to manage the rigidity gradients to the proximal portion of the microlead. An example of an implementation of this lead is shown in FIG. 15c.

One skilled in the art will appreciate that the present invention can be practiced by embodiments other than those described herein, which are provided for purposes of illustration and explanation, and not of limitation.

The invention claimed is:

1. A lead for sensing / pacing for implantation in venous, arterial or lymphatic networks, comprising a proximal end and a distal end, said distal end comprising an active part including a microcable having a diameter of at most equal to 2 French (0.66mm), said microcable comprising:
    an electrically conductive core cable having a diameter of at most equal to 0.50 mm, said core cable comprising a plurality of strands each having a diameter of at most equal to 40µm, said core cable comprising a structuring material having a high fatigue strength, and;
    an polymer insulation layer at least partially surrounding the core cable and having a thickness of at most equal to 30% of the diameter of the core cable, wherein:
    the core cable of the microcable comprises a composite structure formed from at least (i) said structuring material and (i) a radiopaque material constituting at least about 0.008mm² of the core cable section cross section in an amount of at most 50%, wherein the conductive core cable is comprised of multiple strands in which individual a first set of strands are formed from the structuring material and a second set of strands are formed from the radiopaque material, and
    at least one denuded area is formed in the insulation layer so as to form at least one electrode having a cumulative total surface areas of at most 20mm²; and
    means for gradually reducing a rigidity along the lead between its proximal end portion and its distal end.

2. The lead of claim 1, wherein the microcable further comprises at least one preshape at the electrodes for electrical contact and mechanical stabilization.

3. The lead of claim 1, wherein each of said plurality of strands further comprises a diameter of between 20 and 40μm.

4. The lead of claim 1, wherein said structuring material is a material selected from among the group consisting of: stainless steel, a cobalt alloy, a precious metal, titanium or an NiTi alloy.

5. The lead of claim 1, wherein the radiopaque material is a material selected from among the group consisting of: tantalum (Ta), tungsten (W), iridium (Ir), platinum (Pt), gold (Au) and their alloys.

6. The lead of claim 1, wherein said plurality of strands comprises between 15 and 300 strands.

7. The lead of claim 1, wherein the polymer isolation layer further comprises a fluropolymer.

8. The lead of claim 1, wherein the plurality of strands comprise an outer layer of material having a low magnetic susceptibility of less than $2\,000 \times 10^{-12}$ $m^3$ $mole^{-1}$.

9. The lead of claim 8, wherein the radiopaque material having low magnetic susceptibility is selected from among the group consisting of: tantalum (Ta), titanium (Ti), rhodium (Rh), molybdenum (Mo), tungsten (W), palladium (Pd), gold (Au) and thus alloys.

10. The lead of claim 1, wherein each denuded area forming an electrode further comprises a surface area of at most equal to $0.5mm^2$.

11. The lead of claim 1, further comprises a coating for corrosion resistance disposed on said at least one electrode.

12. The lead of claim 1, further comprising an anti-inflammatory material disposed in the vicinity of the at least one electrode.

13. The lead of claim 1, wherein the material constituting the isolation layer incorporates an anti-inflammatory material.

14. The lead of claim 1, wherein the preshape further comprises an S plane preshape.

15. The lead of claim 1, wherein the preshape further comprises a spiral three-dimensional preshape.

16. The lead of claim 1, further comprising means for locally reinforcing the microcable.

17. The lead of claim 1, wherein the means for gradually decreasing the rigidity further comprises a stepped stack of tubes fitted into each other.

18. The lead of claim 1, wherein the means for gradually decreasing the rigidity further comprises a plurality of isodiameter tubes having different stiffnesses, said isodiameter tubes being disposed in order to provide a succession of decreasing stiffness along said microcable.

19. The lead of claim 1, further comprising a first plurality of microcables associated with a second plurality of independent stimulation current carrying lines.

* * * * *